(12) United States Patent
Wollenweber

(10) Patent No.: US 8,076,644 B2
(45) Date of Patent: Dec. 13, 2011

(54) METHODS AND SYSTEMS FOR DETERMINING A MEDICAL SYSTEM ALIGNMENT

(75) Inventor: Scott David Wollenweber, Waukesha, WI (US)

(73) Assignee: General Electric Company, Schenectady, NY (US)

(*) Notice: Subject to any disclaimer, the term of this patent is extended or adjusted under 35 U.S.C. 154(b) by 50 days.

(21) Appl. No.: 12/629,191

(22) Filed: Dec. 2, 2009

(65) Prior Publication Data

US 2011/0127434 A1 Jun. 2, 2011

(51) Int. Cl.
*G01T 1/166* (2006.01)
(52) U.S. Cl. ............... 250/362; 250/363.03; 250/363.04
(58) Field of Classification Search .......... 250/363.03, 250/363.04, 363.05
See application file for complete search history.

(56) References Cited

U.S. PATENT DOCUMENTS

| | | | |
|---|---|---|---|
| 5,376,796 A * | 12/1994 | Chan et al. | 250/363.04 |
| 5,998,792 A * | 12/1999 | DiFilippo | 250/363.05 |
| 6,556,720 B1 | 4/2003 | Avinash | |
| 6,701,025 B1 | 3/2004 | Avinash | |
| 6,850,585 B2 | 2/2005 | Hsieh et al. | |
| 7,009,396 B2 | 3/2006 | Zhu et al. | |
| 7,016,522 B2 * | 3/2006 | Bani-Hashemi | 382/131 |
| 7,359,540 B2 | 4/2008 | Avinash | |
| 7,428,290 B2 | 9/2008 | Nishide et al. | |
| 2002/0103429 A1 * | 8/2002 | deCharms | 600/410 |
| 2004/0051529 A1 | 3/2004 | Zhu et al. | |
| 2004/0222379 A1 * | 11/2004 | Cook | 250/363.03 |
| 2005/0145798 A1 * | 7/2005 | Stark et al. | 250/363.08 |
| 2007/0280508 A1 * | 12/2007 | Ernst et al. | 382/107 |
| 2007/0290125 A1 * | 12/2007 | Wang et al. | 250/252.1 |
| 2008/0103391 A1 * | 5/2008 | Dos Santos Varela | 600/436 |
| 2008/0230704 A1 * | 9/2008 | Daghighian | 250/363.03 |

\* cited by examiner

*Primary Examiner* — David Porta
*Assistant Examiner* — Marcus Taningco
(74) *Attorney, Agent, or Firm* — Dean D. Small; The Small Patent Law Group

(57) ABSTRACT

Methods and systems for performing a patient scan using a three-dimensional (3D) cylindrical Positron Emission Tomography (PET) imaging system are provided. The method includes acquiring a count-rate profile of a brain, repositioning at least one of a detector and the brain based on the count-rate profile and a detector sensitivity profile, and scanning the brain when the acquired count-rate profile substantially matches the detector sensitivity profile.

20 Claims, 5 Drawing Sheets

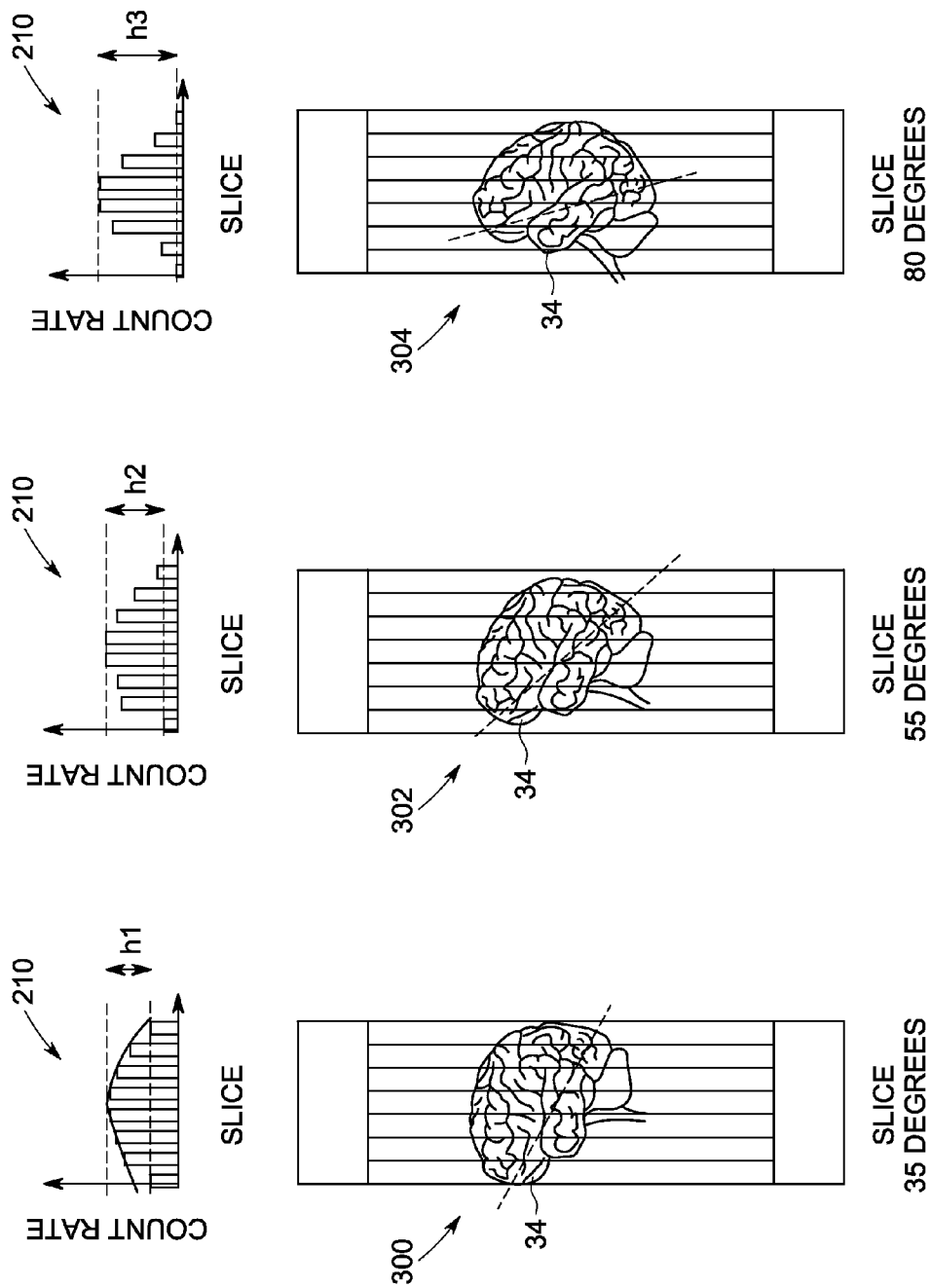

METHODS AND SYSTEMS FOR DETERMINING A MEDICAL SYSTEM ALIGNMENT

BACKGROUND OF THE INVENTION

The subject matter disclosed herein relates generally to imaging systems, and more particularly, embodiments relate to systems and methods for determining an alignment for a medical imaging system.

Positron Emission Tomography (PET) and Single Photon Emission Computed Tomography (SPECT) systems scan objects to acquire image information, in particular physiological information. During operation of a PET or SPECT imaging system, for example, a patient is initially injected with a radiopharmaceutical. After some period of time, the patient is positioned within the imaging system and a scan of the patient is performed.

The patient must be properly positioned within the imaging system in order to acquire the image information. Specifically, if a patient is not properly aligned with respect to the medical imaging system, the organ of interest may not be within the field of view of the imaging system. In this case, the patient is repositioned and the scanning operation is repeated. This process may be performed multiple times if patient positioning is inadequate. Repeatedly repositioning the patient with respect to the medical imaging system increases both the duration of the overall scanning procedure and may increase patient discomfort.

BRIEF DESCRIPTION OF THE INVENTION

In one embodiment, a method for performing a patient scan using a three-dimensional (3D) cylindrical Positron Emission Tomography (PET) imaging system is provided. The method includes acquiring a count-rate profile of a brain, repositioning at least one of a detector relative to the brain based on the count-rate profile and a detector sensitivity profile, and scanning the brain when the acquired count-rate profile substantially matches the detector sensitivity profile.

In another embodiment, a three-dimensional (3D) Positron Emission Tomography (PET) imaging system is provided. The PET imaging system includes a cylindrically-shaped (ring) detector geometry and a detector alignment module coupled to the ring detector. The detector alignment module is programmed to receive a count-rate profile of a brain, reposition a ring detector based on the count-rate profile and a detector sensitivity profile, and scan the brain when the acquired count-rate profile substantially matches the detector sensitivity profile.

In a further embodiment, a computer readable medium is provided. The computer readable medium is encoded with a program to instruct a computer to receive a count-rate profile of a brain, reposition a ring detector based on the count-rate profile and a detector sensitivity profile, and scan the brain when the acquired count-rate profile substantially matches the detector sensitivity profile.

BRIEF DESCRIPTION OF THE DRAWINGS

FIG. 6 is a diagram illustrating an exemplary count-rate profile acquired in accordance with various embodiments of the present invention.

FIG. 7 is a diagram illustrating another exemplary count-rate profile acquired in accordance with various embodiments of the present invention.

FIG. 8 is a diagram illustrating another exemplary count-rate profile acquired in accordance with various embodiments of the present invention.

DETAILED DESCRIPTION OF THE INVENTION

Figure 1:
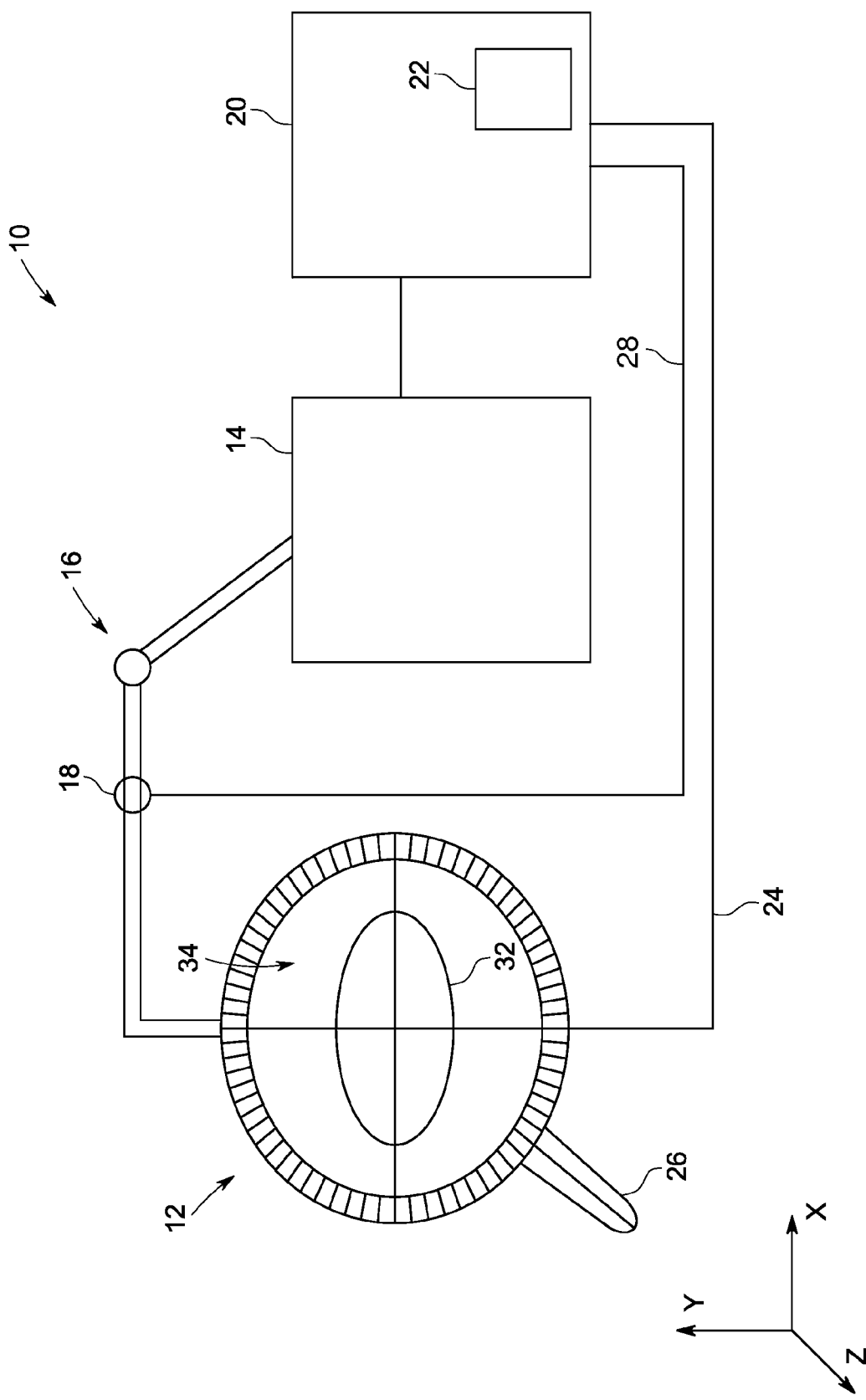
FIG. 1 is a simplified block diagram of an exemplary imaging system formed in accordance with various embodiments of the present invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like), or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

FIG. 1 is a schematic block diagram of an exemplary imaging system 10 formed in accordance with various embodiments described herein. In the exemplary embodiments, the imaging system 10 is a Nuclear Medicine (NM) imaging system, for example, a Positron Emission Tomography (PET) imaging system that includes cylindrically-dispositioned (ring) detectors. Optionally, the imaging system 10 may be a Single Photon Emission Computed Tomography (SPECT) imaging system.

In the exemplary embodiment, the imaging system 10 is a three-dimensional (3D) cylindrical Positron Emission Tomography (PET) imaging system that is configured to image a brain of an exemplary patient. The imaging system 10 includes a ring detector 12 that is coupled to or supported by a gantry 14. The ring detector 12 includes a plurality of individual detector elements to enable the imaging system 10 to acquire and reconstruct 3D images of the patient's brain. In one embodiment, the ring detector 12 is configured, e.g. sized and shaped, to be positioned over a patient's head to enable the imaging system 10 to scan the patient's brain. Optionally, the patient may be repositioned with respect to the imaging system 10. For example, the imaging system 10 may include a bed configured to receive the patient. During various imaging procedures the bed may be repositioned, thus repositioning the patient with respect to a stationary detector.

In the exemplary embodiment, an articulated arm 16 is operated to facilitate repositioning of the ring detector 12 with respect to the patient. In this exemplary embodiment, the articulated arm 16 may be moved in any direction, for example, an x-direction, a y-direction, and/or a z-direction, or in combinations thereof. More specifically, the articulated arm 16 is movable arm vertically upward and downward away from or towards a patient's head to enable the ring detector 12 to be positioned for imaging the patient's brain. Accordingly, the articulated arm 16 may be configured for pivoting movement to enable the articulated arm 16 to be moved closer to or away from the patient. The articulated arm 16 allows the ring detector 12 to be positioned at any horizontal or vertical position. The imaging system 10 may also include an encoder 18 that is mounted to the articulated arm 16 to provide position information as feedback for controlling the movement of the articulated arm 16. The feedback information may be communicated through a communication link 24 to a computer 20 configured to control the movement of the articulated arm 16 and thus control the positioning of the ring detector 12. As used herein, the term "computer" may include any processor-based or microprocessor-based system including systems using microcontrollers, reduced instruction set computers (RISC), application specific integrated circuits (ASICs), field programmable gate array (FPGAs), logic circuits, and any other circuit or processor capable of executing the functions described herein. The above examples are exemplary only, and are thus not intended to limit in any way the definition and/or meaning of the term "computer". In the exemplary embodiment, the computer 20 executes a set of instructions that are stored in one or more storage elements or memories, in order to process input data. The storage elements may also store data or other information as desired or needed. The storage element may be in the form of an information source or a physical memory element within the scanner controller 46.

In the exemplary embodiment, the imaging system 10 also includes a detector positioning alignment module 22. In one embodiment, the detector alignment module 22 is implemented as a set of instructions on the computer 20. The set of instructions may include various commands that instruct a scanner controller (shown in FIG. 2) to perform specific operations such as repositioning the articulated arm 16, which may be motorized. The instructions also may include, for example, commands that control the operation and positioning of the ring detector 12, via the articulated arm 16, based on information received from the encoder 18. The set of instructions may also include commands that control the operation and positioning of the ring detector 12, via the articulated arm 16, based on information input from an operator. The set of instructions may be in the form of a software program.

The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

Another embodiment includes an active graphical display of the ring detector per-ring count-rate and use of user-activated ring detector alignment controls, enabling user-controllable scan alignment.

Referring again to FIG. 1, the imaging system 10 also includes the communication link 24 that connects or communicates information from the ring detector 12 to the computer 20. The information may include for example, emission data generated by a plurality of detector elements 26 during a medical scanning procedure. The imaging system 10 also includes at least one communication link 28 that connects the encoder 18 to the computer 20 and/or the detector alignment module 22, and a communication link 30 that connects the computer 20 to the gantry 14 to enable the computer 20 to control the operation, movement, and position of the ring detector 12.

Figure 2:
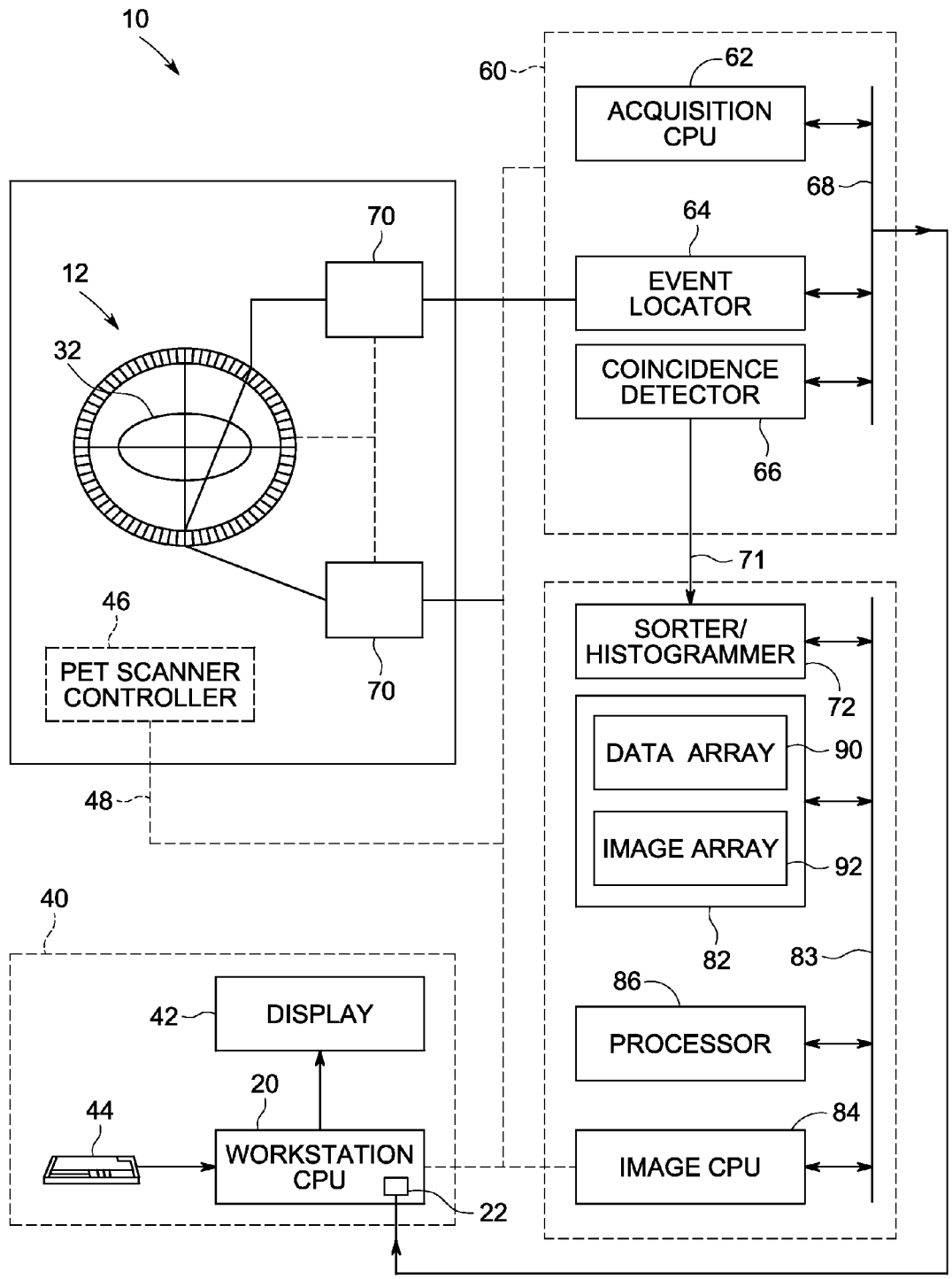
FIG. 2 is a detailed block schematic diagram of the system illustrated in FIG. 1 formed in accordance with various embodiments of the present invention.

FIG. 2 is a detailed block schematic diagram of the exemplary imaging system 10 shown in FIG. 1 in accordance with various embodiments of the present invention. In the exemplary embodiment, the imaging system 10 includes an operator workstation 40. The operator workstation 40 includes the computer 20, a display 42 and an input device 44. During operation, the workstation 40, via the computer 20, is programmed to control the movement of the ring detector 12 via a scanner controller 46. A communication link 48 may be hardwired between the PET scanner controller 46 and the workstation 40. Optionally, the communication link 48 may be a wireless communication link that enables information to be transmitted to or from the workstation 40 to the PET scanner controller 46 wirelessly. In the exemplary embodiment, the workstation 40 controls real-time operation of the PET imaging system 10. The workstation 40 may also be configured to perform the methods described herein.

In the exemplary embodiment, the imaging system 10 also includes a data acquisition processor 60 that includes at least an acquisition CPU or computer 62. The data acquisition processor 60 also includes an event locator circuit 64 and a coincidence detector 66. The acquisition CPU 62 controls communications on a back-plane bus 68 and on a communication link 71. During operation, the data acquisition processor 60 periodically samples digital signals produced by a pair of acquisition circuits 70. The digital signals produced by the acquisition circuits 70 are transmitted to the event locator circuit 64. The event locator circuit 64 processes the information to identify each valid event and provide a set of digital numbers or values indicative of the identified event. For example, this information indicates a detector element recording the event and the time the detector element began counting the event. Moreover, the event locator circuit 64 may also transmit information to the alignment module 22. The alignment module 22 utilizes the event information to align the ring detector 12 with respect to the brain 32. The events are also counted to form a record of the single channel events recorded by each detector element. An event data packet is communicated to the coincidence detector 66 through the back-plane bus 68.

The coincidence detector 66 receives the event data packets from the event locator circuit 64 and determines if any two of the detected events are in coincidence. Coincident event pairs are located and recorded as a coincidence data packets by the coincidence detector 66 and are communicated through the back-plane bus 68 to the detector alignment module 22. The output from the coincidence detector 66 is referred to herein as an emission data set or raw image data. In one embodiment, the emission data set may be stored in a memory device that is located in the data acquisition processor 60. Optionally, the emission data set may be stored in the workstation 40.

The imaging system 10 may also include a sorter/histogrammer 72 to generate a data structure known as a histogram. In the exemplary embodiment, the sorter/histogrammer 72 is configured to generate various histograms described herein. Optionally, the workstation 40 may be configured to generate the histograms described herein. An image reconstruction processor 61 includes the sorter/histogrammer 72, a memory module 82, an image CPU 84, an array processor 86, and a communication bus 88. During operation, the sorter/histogrammer 72 performs motion related histogramming described in more detail below and generates the events listed in the image data subset into 3D data. This 3D data, or sinograms, is organized in one exemplary embodiment as a data array 90. The data array 90 is stored in the memory module 82.

The communication bus 88 is linked to the back-plane bus 68 through the image CPU 84. The image CPU 84 controls communication through communication bus 88. The array processor 86 is also connected to the communication bus 88. The array processor 86 receives the data array 90 as an input and reconstructs images in the form of image arrays 92. Resulting image arrays 92 are then stored in the memory module 82. The images stored in the image array 92 are communicated by the image CPU 84 to the operator workstation 40.

In operation, the imaging system 10 is configured to position the ring detector 12 with respect to the patient's brain 32. More specifically, for a cylindrical PET imaging system, such as imaging system 10 shown in FIG. 1, there are multiple imaging system positions wherein the ring detector 12 may be positioned to image the brain 32. In the exemplary embodiment, there is a single optimal imaging position wherein the brain 32 may be positioned with respect to the ring detector 12 such that a sensitivity profile of the ring detector 12 substantially matches the count-rate profile of the emission data acquired from a scan of the brain 32.

Figure 3:
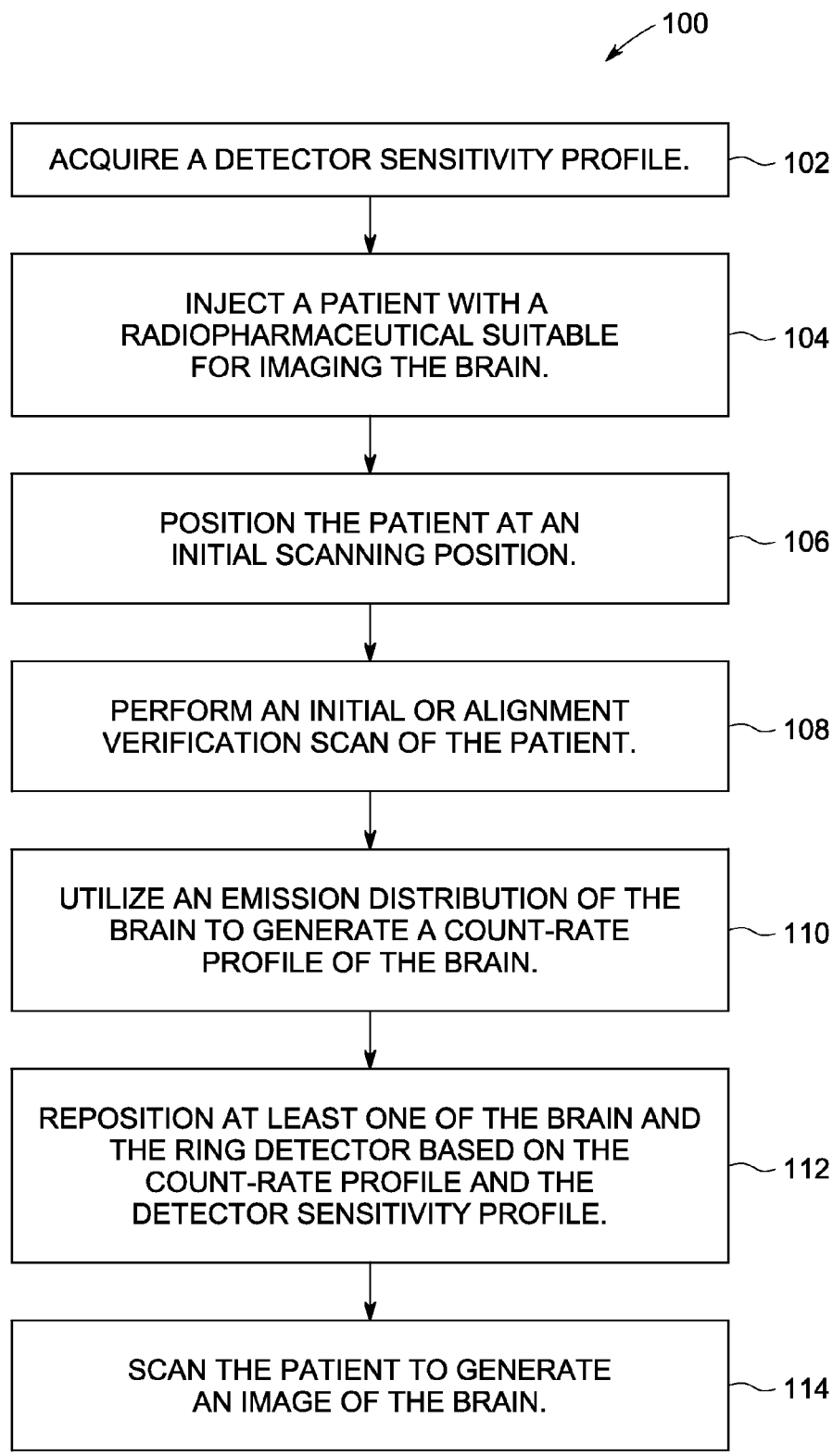
FIG. 3 is a flowchart of an exemplary method for performing a scan in accordance with various embodiments of the present invention.

FIG. 3 is a block diagram of an exemplary method 100 for performing a patient scan using a 3D PET imaging system including a ring detector. In the exemplary embodiment, the method 100 is performed using the PET imaging system 10 including the ring detector 12, shown in FIGS. 1 and 2.

The methods described herein may be implemented as a set of instructions that include various commands that instruct the computer or processor 20 as a processing machine to perform specific operations such as the methods and processes of the various embodiments described herein. For example, portions of the method 100 may be implemented as a set of instructions in the form of a software program that is installed on or implemented by the detector alignment module 22. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Figure 4:
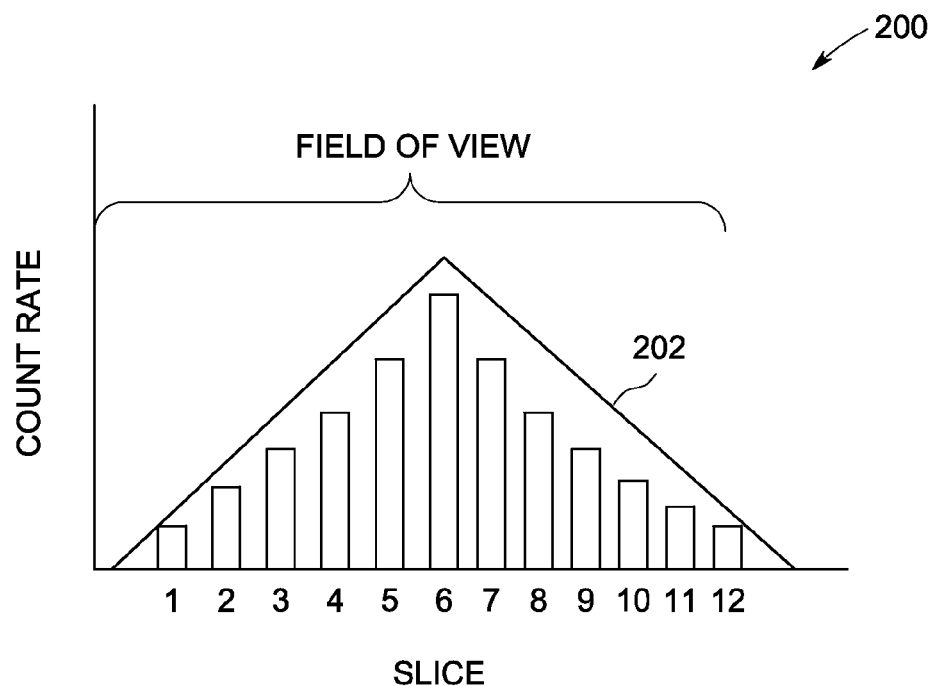
FIG. 4 is an exemplary detector sensitivity profile generated in accordance with various embodiments of the present invention.

Referring again to FIG. 3, at 102 a detector sensitivity profile is acquired. The detector sensitivity profile optionally may be pre-determined and loaded from a computer for use by the method 100. More specifically, the detector sensitivity profile may be determined based on actual measurements of the ring detector. Optionally, the detector sensitivity profile may be determined based on a priori knowledge of the ring detector. An axial detector sensitivity profile represents the axial count distribution expected to be received as a function of axial location within the detector. FIG. 4 illustrates an exemplary detector sensitivity profile 200 wherein the X-axis represents image axial slices and the Y-axis represents the count distribution expected to be recorded for each image slice when imaging a uniform axial source distribution in a ring detector. For example, assuming that the ring detector 12 includes twelve rows of detector elements, and thus twelve slices, the detector sensitivity profile 200 illustrates the counts recorded for each respective slice. In the exemplary embodiment, the detector sensitivity profile 200 is represented as a histogram that may be visually displayed to an operator, for example, on the display 42. Optionally, the detector sensitivity profile 200 may be stored in the computer and utilized by an algorithm discussed in more detail below. In the exemplary embodiment, the detector sensitivity profile 200 has a substantially triangular shape. More specifically, during a scanning operation, the slices nearer a center of a field-of-view are geometrically more sensitive to photons and thus are expected to record more counts and the slices nearer the edge of the FOV are geometrically less sensitive. In the exemplary embodiment, for a ring detector, such as ring detector 12, a detector sensitivity profile 200 has a triangular shape 202. Whereas, an alternative system (SPECT or collimated PET imaging system) may have a trapezoidal shaped sensitivity profile. It should be realized that a detector sensitivity profile is typically unique for each detector based on the size and geometry of the detector. In the exemplary embodiment, the detector sensitivity profile 200 may be acquired by accessing the detector sensitivity profile stored in the computer 20. Optionally, the detector sensitivity profile may be acquired from the operator itself based on a prior knowledge. For example, the operator may be knowledgeable of the shape of the detector sensitivity profile for the imaging system being utilized to scan the patient. It should be noted that optimization between the alignment of a detector sensitivity profile and a target organ to be imaged will optimize the acquisition of detected counts per unit time, which is correlated to resultant data (image) quality.

Referring again to FIG. 3, at 104, a patient is injected with a radiopharmaceutical suitable for imaging the brain 32. After a predetermined time period, at 106, the patient is positioned to at an initial scanning position. In one embodiment, the patient may be positioned in a horizontal position such that the patient is in a supine position on an imaging table. In the exemplary embodiment, the patient is positioned in an upright or sitting position.

At 108, an initial or alignment verification scan of the patient is performed to generate an emission distribution of the brain. To perform the initial alignment verification, the detector alignment module 22 is configured to position the ring detector 12 with respect to the patient' head such the patient's brain 32 is disposed substantially within a central opening 34 of the ring detector 12. The ring detector 12 may be repositioned using the articulated arm 16 described above. Optionally, the ring detector 12 may be manually positioned over the patient's head.

As discussed above, during operation of the PET imaging system, for example imaging system 10, after a patient is initially injected with a radiopharmaceutical, the radiopharmaceutical emits positrons as the radiopharmaceutical decays at 104. The emitted positrons travel a relatively short distance before the positrons encounter an electron, at which point an annihilation occurs, whereby the electron and positron are annihilated and converted into two gamma photons each having an energy of 511 keV.

The annihilation events are typically identified by a time coincidence between the detection of the two 511 keV gamma photons in the two oppositely disposed detectors, i.e., the gamma photon emissions are detected virtually simultaneously by each detector. When two oppositely disposed gamma photons each strike an oppositely disposed detector to produce a time coincidence, gamma photons also identify a line of response (LOR) along which the annihilation event has occurred.

The detected rate of paired event time coincidences, generally referred to as coincidence events, detected within a field of view (FOV) of the detector is the count rate of the detector. The count rate at each of two oppositely disposed detectors is generally referred to as singles count rate, or singles rate. A coincidence event is identified if the time difference between the arrivals of signals at the oppositely disposed detectors is less than a predetermined time coincidence. The number of coincidence events per second registered is commonly referred to as prompt coincidence rate or prompts rate. Prompts may include true, random, and scatter coincidence events. The emissions emitted from the patient's brain, including true, random, and scatter coincidence events are referred to herein as the emitted distribution. It should be realized that the emitted distribution from the brain depends upon the geometry of the specific brain being imaged among other factors. Moreover, the emitted distribution depends on the biodistribution of the radiopharmaceutical that typically varies from patient to patient.

Figure 5:
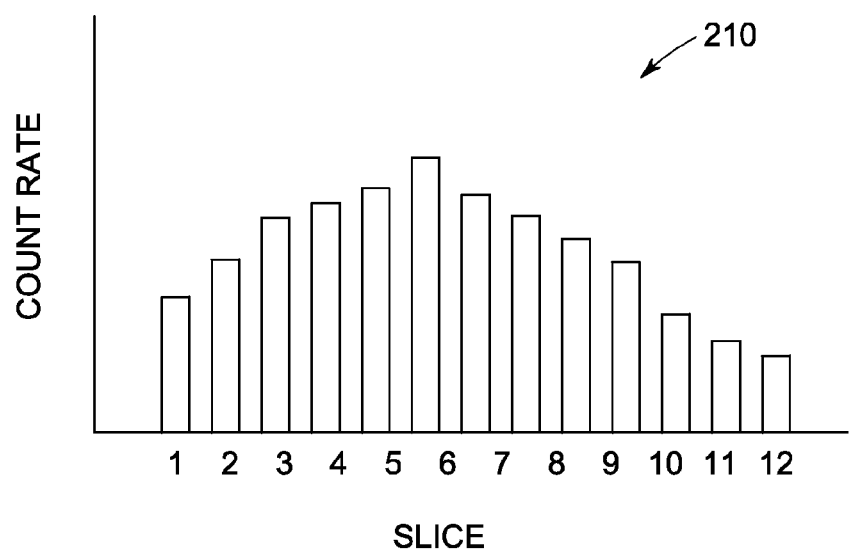
FIG. 5 is an exemplary count-rate profile generated in accordance with various embodiments of the present invention.

At 110, the emission distribution of the brain 32 is used to generate a count-rate profile of the brain. A count-rate profile represents the counts received from the brain based on the emitted distribution, or count rate, for detected events within each axial slice in the ring detector 12. A count-rate profile provides a visual representation of the alignment of the brain 32 to the detector based upon the emitted distributions emitted from the brain 32. FIG. 5 illustrates an exemplary count-rate profile 210 generated at 110 wherein the X-axis represents the image axial slice and the Y-axis represents the counts recorded per slice. For example, assuming that the ring detector 12 includes twelve rows of detector elements, and thus twelve slices, the count-rate profile 210 illustrates twelve slices along the X-axis. Moreover, the count-rate profile 210 illustrates the counts recorded for each respective slice. In the exemplary embodiment, the count-rate profile 210 is represented as a histogram that is visually displayed to an operator, for example, on the display 42. Moreover, during an initial or alignment verification scan, the count-rate profile is continuously updated to enable to the operator to observe and reposition the brain 32, in real-time as is discussed in more detail below. In the exemplary embodiment, the count-rate profile 210 is updated in real-time, for example, at least once per second, during the pre-scan.

At 112, at least one of the brain 32 and the ring detector 12 is repositioned based on the count-rate profile 210 and the detector sensitivity profile 200. In the exemplary embodiment, the brain 32 is repositioned until the count-rate profile 210 of the brain 32 substantially matches the detector sensitivity profile 200. As discussed above, in the exemplary embodiment, the ring detector 12 has a sensitivity profile 200 that is substantially triangular in shape. Accordingly, in the exemplary embodiment, at 112, at least one of the brain 32 and the ring detector 12 are repositioned until the count-rate profile 210 has the most triangular shape measured that substantially matches the triangular shape of the detector sensitivity profile. Continuously updating the count-rate profile 210 enables the operator to visually observe the effects of moving the ring detector 12. For example, the operator may move the ring detector 12 in a first axial direction and then observe if the count-rate profile 210 more closely approximates the detector sensitivity profile 200. In this case, the operator may choose to continue moving the ring detector 12 in the first axial direction until the count-rate profile 210 substantially matches the detector sensitivity profile 200. Determining when the count-rate profile 210 substantially matches the detector sensitivity profile 200 may be based on the operator's judgment. Optionally, the algorithm may include a matching feature that automatically determines when the count-rate profile 210 is within a predetermined range.

For example, FIG. 6 illustrates a histogram of the count-rate profile 210 acquired at an initial imaging position 300 wherein the brain 32 has been positioned inside the ring detector 12 at an angle (OM line—dashed) of approximately 35 degrees. As shown in FIG. 6, the count-rate profile 210 for the initial imaging position 300 has a substantially trapezoidal shape. It should be also be realized that the count-rate profile 210 is continuously updated and visually displayed in real-time to the operator on the display 42. As such, the operator may continuously reposition while observing the updated count-rate profile 210 on the display 42.

In one embodiment, the operator may visually inspect the count-rate profile 210 to determine if the count-rate profile 210 has a shape that substantially matches the triangular shape of the detector sensitivity profile 200 shown in FIG. 4. For example, the operator may direct that the detector sensitivity profile 200 be displayed on the display 42. The operator may also direct the count-rate profile 210 to be displayed alongside the detector sensitivity profile 200. In this arrangement, the operator may visually determine whether the shape of the count-rate profile 210 substantially matches the shape of the detector sensitivity profile 200. Optionally, the triangular shape of the detector sensitivity profile 200 may be overlayed onto the count-rate profile 210.

In another embodiment, the computer 40 may include an algorithm that automatically determines the shape of the count-rate profile 210 and also determines whether the shape of the count-rate profile 210 substantially matches the shape of the detector sensitivity profile 200. For example, the algorithm may average the end slices to determine the shape of the count-rate profile 210. The calculated shape of the count-rate profile 210 is then compared to the detector sensitivity profile 200 stored in the computer 40. The algorithm may then output a value that represents the degree of the match. For example, the algorithm may output a 1 indicating that there are substantial differences between the shape of the detector sensitivity profile 200 and the count-rate profile 210. More specifically, a value of 1 may indicate that the count-rate profile 210 has a trapezoidal shape that does not closely match the triangular shape of the detector sensitivity profile 200. Whereas, a value of 10 may indicate that the count-rate profile 210 has a triangular shape that closely matches the triangular shape of the detector sensitivity profile 200.

In the exemplary embodiment, assuming that the count-rate profile 210 does not closely match the detector sensitivity profile 200, the operator may reposition at least one of the brain 32 and the ring detector 12. In the exemplary embodiment, the operator repositions the ring detector 12 using the detector positioning alignment module 22 described above. Optionally, the operator may manually reposition the ring detector 12. As the ring detector 12 is repositioned, the count-rate profile is continuously updated and displayed on the display 42.

For example, FIG. 7 illustrates a histogram of the count-rate profile 210 acquired at a second imaging orientation 302 wherein the brain 32 has been positioned inside the ring detector 12 at an angle (OM line—dashed) of approximately 55 degrees. As shown in FIG. 7, the count-rate profile 210 for the second imaging position 302 has a shape that is between a trapezoidal shape and a triangular shape. More specifically, repositioning the brain 32 from the initial imaging position 300 to the second imaging position 302 results in a count-rate profile that more closely approximates the detector sensitivity profile 200. However, in this embodiment, the count-rate profile acquired in the second imaging position 302 still may not optimally match the detector sensitivity profile 200. This determination may be made visually or using the algorithm as discussed above.

FIG. 8 illustrates a histogram of the count-rate profile 210 acquired at a third imaging position 304 wherein the brain 32 has been positioned inside the ring detector 12 at an angle of approximately 80 degrees. As shown in FIG. 8, the count-rate profile 210 for the third imaging position 304 has a shape that more closely matches the shape of the detector sensitivity profile 200. More specifically, repositioning the brain 32 from the initial imaging position 300 to the third imaging position 304 results in a count-rate profile that more closely approximates the detector sensitivity profile 200. Specifically, the count-rate profile 210 acquired at the third imaging position 304 has a triangular shape that closely matches the triangular shape of the detector sensitivity profile 200. This determination may be made visually or using the algorithm as discussed above. It should be realized that the angles of 35 degrees, 55 degrees, and 80 degrees are merely exemplary to facilitate explaining the operation of the methods and systems described herein and will vary in practice. In the exemplary embodiment, the brain 32 or the ring detector 12 are repositioned at step 110 until the emitted distribution of the brain most closely matches the detector sensitivity profile 200. More specifically, the method at 110 is an iterative process that is repeated until the position of the brain 32 is optimally aligned with the ring detector 12. When the optimal alignment position is determined at 112, at 114 the patient is scanned with the imaging system 10 to generate an image of the brain 32.

Described herein are various methods and systems that perform a scan of a patient's brain. The various systems are configured to reposition the detector based on a count-rate profile to improve the imaging geometry. Accordingly, the patient may remain in a comfortable sitting position during the scanning procedure. A technical effect of the various embodiments described herein is to utilize a count-rate profile that represents the emission distribution of the brain to reposition the detector. In the exemplary embodiment, the emission distribution provides an optimal information source for determining the proper alignment of the brain within the ring detector. Moreover, the various systems and methods described herein utilize the information that for a cylindrical PET imaging system, the sensitivity profile detected in any given slice as a function of slice number is substantially triangular. More specifically, the end slices are the least sensitive geometrically and the center slices are the most sensitive geometrically. Brain to ring detector alignment is achieved when the brain is positioned at the axial and transaxial centers of the ring detector because the ring detector is most sensitive at this point in the exemplary embodiment (3D PET). That is, the probability that an annihilation event occurring at this center location will produce two photons which both strike the ring detector is the highest at this point. As a result, a brain that is centered about the scanner center of a ring detector results in improved data.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of performing a patient scan using a three-dimensional (3D) cylindrical Positron Emission Tomography (PET) imaging system including a detector, said method comprising:
   acquiring a count-rate profile of a brain;
   repositioning at least one of a detector and the brain based on the count-rate profile and a detector sensitivity profile; and
   scanning the brain when the acquired count-rate profile substantially matches the detector sensitivity profile.

2. A method in accordance with claim 1 further comprising utilizing an emitted photon distribution of the brain to acquire the count-rate profile.

3. A method in accordance with claim 1 further comprising:
   acquiring a real-time count-rate profile of a brain; and
   displaying the real-time count rate profile on a display.

4. A method in accordance with claim 1 further comprising visually determining when the acquired count-rate profile substantially matches the sensitivity profile of a detector.

5. A method in accordance with claim 1 further comprising utilizing an algorithm to determine when the acquired count-rate profile substantially matches the sensitivity profile of a detector.

6. A method in accordance with claim 1 wherein the detector has a substantially triangular-shaped sensitivity profile, said method further comprising repositioning the brain until the acquired count-rate profile substantially matches a ring detector sensitivity profile.

7. A method in accordance with claim 1 further comprising automatically repositioning a ring detector until the acquired count-rate profile substantially matches a sensitivity profile of the ring detector.

8. A method in accordance with claim 1 further comprising:
positioning a patient in a sitting position, and
acquiring a count-rate profile of a brain while the patient is in the sitting position.

9. A method in accordance with claim 1 further comprising:
acquiring the count-rate profile of the brain during a pre-scan; and
performing a second scan when the acquired count-rate profile substantially matches the sensitivity profile of the detector, the pre-scan being conducted for a first time, the second scan being conducted for a second time that is greater than the first time.

10. A method in accordance with claim 1 further comprising repositioning at least one of the detector and the brain until the acquired count-rate profile has a substantially triangular shape that substantially matches a sensitivity profile of the detector.

11. A method in accordance with claim 1 further comprising:
acquiring a count-rate profile of the brain that is based on an emitted photon distribution of the brain;
generating at least one histogram that is based on the count-rate profile; and
visually determining when the count-rate profile substantially matches the detector sensitivity profile using the at least one histogram.

12. A three-dimensional (3D) Positron Emission Tomography (PET) imaging system comprising a ring detector and a detector alignment module coupled to the ring detector, wherein the detector alignment module is programmed to:
receive a count-rate profile of a brain;
reposition a ring detector based on the count-rate profile and a detector sensitivity profile; and
scan the brain when the acquired count-rate profile substantially matches the detector sensitivity profile.

13. A PET imaging system in accordance with claim 12, wherein the ring detector is configured to generate a count-rate profiled based on an emitted photon distribution of the brain.

14. A PET imaging system in accordance with claim 12, wherein the PET imaging system is further configured to:
acquire a real-time count-rate profile of a brain; and
display the real-time count rate profile on a display.

15. A PET imaging system in accordance with claim 12, wherein the detector alignment module is further programmed to determine when the acquired count-rate profile substantially matches the detector sensitivity profile.

16. A PET imaging system in accordance with claim 12, wherein the detector alignment module is further programmed to reposition a ring detector until the acquired count-rate profile acquired from the ring detector substantially matches a triangular-shaped sensitivity profile of the ring detector.

17. A PET imaging system in accordance with claim 12, wherein the detector alignment module is further programmed
acquire the count-rate profile of the brain during a pre-scan; and
initiate a second scan when the acquired count-rate profile substantially matches the sensitivity profile of the ring detector, the second scan being conducted for a time that is greater than a time used to conduct the pre-scan.

18. A non-transitory computer readable medium encoded with a program to instruct a computer to:
receive a count-rate profile of a brain;
reposition a ring detector based on the count-rate profile and a detector sensitivity profile; and
scan the brain when the acquired count-rate profile substantially matches the detector sensitivity profile.

19. A non-transitory computer readable medium in accordance with claim 18 wherein the program further instructs a computer to generate a count-rate profiled based on an emitted photon distribution of the brain.

20. A non-transitory computer readable medium in accordance with claim 18 wherein the program further instructs a computer to:
acquire a real-time count-rate profile of a brain; and
display the real-time count rate profile on a display.

* * * * *